United States Patent [19]

Baird

[11] Patent Number: 5,006,394

[45] Date of Patent: Apr. 9, 1991

[54] MULTILAYER POLYMERIC FILM

[75] Inventor: James C. Baird, Cincinnati, Ohio

[73] Assignee: The Procter & Gamble Company, Cincinnati, Ohio

[21] Appl. No.: 211,518

[22] Filed: Jun. 23, 1988

[51] Int. Cl.$^5$ ................................................ B32B 3/10
[52] U.S. Cl. .................................... 428/138; 428/516; 428/520; 428/284; 428/913
[58] Field of Search ............... 428/516, 520, 131, 913, 428/138, 284

[56] References Cited

U.S. PATENT DOCUMENTS

| | | | |
|---|---|---|---|
| 2,418,907 | 4/1947 | Schreiber | 128/284 |
| 2,690,415 | 9/1954 | Shuler | 167/84 |
| 3,154,461 | 10/1964 | Johnson | 161/116 |
| 3,340,875 | 9/1967 | Dudley et al. | 128/290 |
| 3,408,226 | 10/1968 | McKee et al. | 117/138.8 |
| 3,416,523 | 12/1968 | Yeremian | 128/156 |
| 3,585,998 | 6/1971 | Hayford et al. | 128/284 |
| 3,843,478 | 10/1974 | Zuscik | 161/164 |
| 3,875,942 | 4/1975 | Roberts et al. | 128/287 |
| 3,900,670 | 8/1975 | Ikeda et al. | 428/308 |
| 3,929,135 | 12/1975 | Thompson | 128/287 |
| 4,076,570 | 2/1978 | Medley et al. | 156/244 |
| 4,076,895 | 2/1978 | Theno | 428/516 |
| 4,151,240 | 4/1979 | Lucas et al. | 264/504 |
| 4,303,708 | 12/1981 | Gebhardt et al. | 428/35 |
| 4,321,924 | 3/1982 | Ahr | 128/287 |
| 4,324,246 | 4/1982 | Mullane et al. | 128/287 |
| 4,342,314 | 8/1982 | Radel et al. | 128/287 |
| 4,364,989 | 12/1982 | Moyle | 428/216 |
| 4,390,573 | 6/1983 | Bullard et al. | 428/35 |
| 4,392,862 | 7/1983 | Marsan et al. | 604/366 |
| 4,416,942 | 11/1983 | DiLuccio | 428/332 |
| 4,438,171 | 3/1984 | Wefer | 428/215 |
| 4,444,827 | 4/1984 | Swaroop | 428/216 |
| 4,464,426 | 8/1984 | Anthony | 428/35 |
| 4,521,437 | 6/1985 | Storms | 426/130 |
| 4,524,099 | 6/1985 | DiLuccio | 428/213 |
| 4,525,410 | 6/1985 | Hagiwara et al. | 428/198 |
| 4,526,823 | 7/1985 | Farrell et al. | 428/516 |
| 4,552,709 | 11/1985 | Koger, II et al. | 264/504 |
| 4,610,925 | 9/1986 | Bond | 428/368 |
| 4,624,666 | 11/1986 | DeRossett et al. | 604/366 |
| 4,663,219 | 5/1987 | Janocha et al. | 428/213 |
| 4,690,679 | 9/1987 | Mattingly, III et al. | 604/383 |
| 4,710,186 | 12/1987 | DeRossett et al. | 604/383 |
| 4,713,068 | 12/1987 | Wang et al. | 604/366 |
| 4,725,481 | 2/1988 | Ostapchenko | 428/213 |

FOREIGN PATENT DOCUMENTS

| | | |
|---|---|---|
| 0158573 | 10/1985 | European Pat. Off. . |
| 0172420 | 2/1986 | European Pat. Off. . |
| 0288041 | 10/1988 | European Pat. Off. . |
| 301491 | 2/1989 | European Pat. Off. . |
| 2850227 | 4/1981 | Fed. Rep. of Germany . |
| 2086342 | 5/1982 | Fed. Rep. of Germany . |
| 2099754 | 12/1982 | United Kingdom . |

OTHER PUBLICATIONS

Co-pending commonly assigned U.S. patent application of Leslie D. Ryan, Mark J. Steinhardt, Milton D. Spahni and James C. Baird, Ser. No. 210,672 filed on 6/23/88-Bicomponent Material.

Primary Examiner—Edith Buffalow
Attorney, Agent, or Firm—E. Kelly Linman; John V. Gorman; Richard C. Witte

[57] ABSTRACT

A polymeric multilayer film structure having a high percentage of fillers is disclosed. The fillers are concentrated in a separate filler containing layer having about 5 to about 20 percent of the thickness of the total multilayer film. The filler containing layer is coextruded with a base layer comprising the balance of the thickness of the multilayer film. By keeping the filler containing layer thin, relative to the total film thickness, a multilayer film having a filler concentration up to about 60 weight percent is achievable without significantly adversely affecting the material properties of the multilayer film structure.

19 Claims, 1 Drawing Sheet

MULTILAYER POLYMERIC FILM

FIELD OF THE INVENTION

This invention relates to polymeric films having one or more fillers and more particularly to multilayer films having high concentrations of fillers. The fillers may include opacifying or whitening pigments.

BACKGROUND OF THE INVENTION

The invention relates to a polymeric multilayer film having a high percentage of pigments, or other fillers. Pigments are often added to a thin polymeric film to increase opacity, whiten the film or otherwise modify the optical properties of the film. Other fillers are added to polymeric films to provide bulk, or otherwise decrease the cost of the film. One problem associated with adding high levels of fillers to a polymeric matrix is the resulting adverse effect on material properties such as tear strength, tensile strength and softness which often occurs. The adverse effect on material properties often constrains the percentage, or concentration, of fillers, such as opacifying and whitening pigments, added to a polymeric film.

For example, U.S. Pat. No. 4,521,437 issued to Storms June 4, 1985, teaches that pigment loadings limited to 15 weight percent can be obtained without adversely affecting the material properties of the film. U.S. Pat. No. 3,154,461 issued to Johnson Oct. 27, 1964 teaches a polymeric film having up to 25 weight percent particulate material. However, this teaching further requires biaxial stretching of the film at a temperature above the polymer second order transition temperature to produce opacity. U.S. Pat. No. 3,900,670, issued to Ikeda et al. Aug. 19, 1975 discloses a multilayer film having 26 to 50 weight percent fillers. However, this reference also requires biaxial stretching to produce opacity as a result of voiding within the film.

The opacity and whiteness of a thin film are, therefore, limited by the concentrations of opacifying and whitening pigments added to the film. Stretching of the film, to cause opacity, adds a step to the manufacturing process which is reflected in increased cost.

BRIEF SUMMARY OF THE INVENTION

It is an object of this invention to produce a thin opaque film having high concentrations of pigments or other fillers and which can be made white. It is also an object of this invention to produce a film which does not have significantly reduced material properties due to the high pigment, or other filler, concentrations. It is further an object of this invention to produce a film which does not require stretching as part of the manufacturing process.

The invention is a polymeric multilayer film comprising at least one base layer comprised substantially of a polymeric material and at least one filler containing polymeric layer substantially continuously joined to the base layer. The filler containing layer has from about 15 to about 60 weight percent fillers substantially uniformly dispersed therein and a thickness not exceeding about 20 percent of the total thickness of the multilayer film.

BRIEF DESCRIPTION OF THE DRAWINGS

While the specification concludes with claims particularly pointing out and distinctly claiming the invention, it is believed the same will be better understood from the following description taken in conjunction with the accompanying drawings wherein the same parts have the same reference numeral and similar, or analogous, parts have reference numerals with the same last digit.

DETAILED DESCRIPTION OF THE INVENTION

Figure 1:
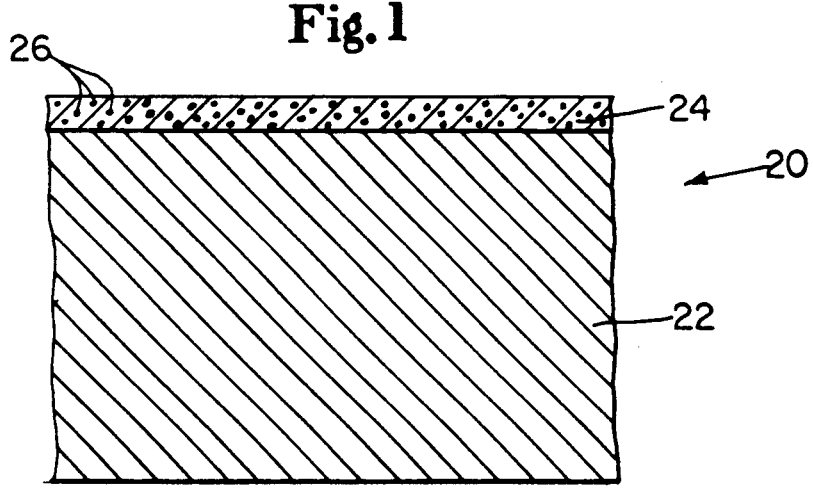
FIG. 1 is a cross sectional view of one embodiment of the multilayer film of the present invention having one base layer and one filler containing layer.

Referring to FIG. 1, the invention comprises a polymeric, multilayer film 20 having at least two layers and a total thickness of typically less than about 0.25 mm (0.01 inches). A first layer 22, the base layer, comprises the substantial thickness, about 80 to about 95 percent, of the multilayer film 20 and is made of conventional polymeric materials. The multilayer film 20 also has a second layer 24 which comprises the balance, less than approximately 20 percent, of the film 20 thickness and which contains a high percentage of fillers 26.

It is important that the base layer 22 be thick relative to the multilayer film 20, comprising from about 80 to about 95 percent of the total thickness of multilayer film 20, and preferably comprising at least nine-tenths of the thickness of the multilayer film 20, so that the material properties of the base layer 22 substantially control the material properties of the multilayer film 20. By maintaining the base layer 22 thick relative to multilayer film 20, the material properties of multilayer film 20 approximate those of base layer 22 and are not significantly adversely affected by the presence of fillers 26 in second layer 24.

The material selected for the base layer 22 must be machinable and capable of being formed into a film. Particular attention should be given to properties after finishing including tear resistance, tensile strength, elastic modulus and any other properties required by the application. If the film 20 is to be used in consumer products which contact the human body, the film 20 must also be soft and safe for epidermal or other human contact. Preferred polymeric materials include polyolefins, particularly polyethylenes, polypropylenes and copolymers having at least one olefinic constituent. Other materials such as polyesters, nylons, copolymers thereof and combinations of any of the foregoing may also be suitable.

If desired, conventional amounts of whiteners (not shown), typically 1 to 15 weight percent, may be added to the polymeric matrix of the first layer 22 to increase its opacity. The percentage of whiteners, such as titanium dioxide and calcium carbonate, are limited by the material properties of the first layer 22, and the application to which the film 20 is used. For example, if the multilayer film 20 of the invention is employed in a diaper or catamenial pad, a first layer 22 having filler levels above approximately 10 weight percent results in a multilayer film 20 which is unpleasant and harsh feeling when placed against the skin.

If desired, the first layer 22 may contain colored pigments instead of whitening pigments. If a first colored pigmentation is employed in first layer 22, and white or a second colored pigmentation in second layer 24, as described below, it is possible to produce a thin film 20 with each side having a different color.

The second layer 24, or polymeric filler containing layer, comprises a polymeric matrix and high concentrations of pigments or other machinable fillers 26. Materials suitable for the second polymeric matrix include polyolefins, such as polyethylenes and polypropylenes, and copolymers having at least one olefinic constituent. Other materials such as polyesters, and nylons, copolymers thereof, and combinations of any of the foregoing may be suitable. Because a flexible and elastic matrix is desirable to accommodate the high concentrations of fillers 26, a relatively softer material such as ethylene vinyl acetate copolymer works well.

To cause opacification, whitening or coloring of second layer 24, approximately 15 to approximately 60 weight percent pigment fillers 26 may be added. Since a film 20 having a whitish appearance, in addition to being opaque, is often desirable, particularly if such film 20 is to be used in disposable consumer products such as catamenial pads, diapers, etc., a whitening o pigment such as titanium dioxide or calcium carbonate may be selected. To achieve a matte surface finish or prevent blocking of the multilayer film 20, a silica filler may be employed in second layer 24. Approximately 50 weight percent fillers 26, substantially equally divided between two types of fillers, one of which is a pigment, has been found to work well. For example, a second layer 24 of ethylene vinyl acetate copolymer having approximately 25 weight percent titanium dioxide and approximately 25 weight percent silica fillers produces a film having a white matte surface. Other useful fillers 25 include colored pigments such as carbon black, etc. To reinforce the multilayer film 20, filament fillers, such as rayon, may be added to second layer 24.

By utilizing light refracting fillers 26, which have a refractive index different than that of the polymeric matrix of second layer 24, a white opaque film 20 can be produced without stretching of the film 20 as part of the manufacturing process. The pigmentation of second layer 24 results from the scattering of light rays refracted from fillers 26, and not as a result of voids created by stretching of film 20. Titanium dioxide, calcium carbonate and silica work well with the polymers described above to cause whitening and opacification by light refraction.

The second layer 24 is thin relative to the total thickness of the multilayer film 20, comprising from about 5 to about 20 percent of the total multilayer film 20 thickness and preferably not more than 10 percent of the total multilayer film 20 thickness. This proportion of layers is important to prevent the second layer 24 from causing the multilayer film 20 to have an excessively brittle or tearable nature. Also, if the second layer 24 is to be placed in contact with the skin, more comfort is provided if the second layer 24 is joined to a more compliant first layer 22 of substantially greater thickness. By keeping the second layer 24 thin relative to the total multilayer film 20, the desirable material properties of the first layer 22 are substantially maintained.

It is necessary that the thickness of the second layer 24 be coordinated with the particle size and percentages of any fillers 26 added to second layer 24. While the second layer 24 is brittle, and easily torn due to the high filler 26 concentrations, the filler particles 26 should not be so large, or the second layer 24 so thin, that the particles 26 are not totally contained by the polymer material of the second layer 24 or protrude through the surface of the second layer 24, otherwise the filler particles 26 may be torn from the polymeric matrix and not provide the desired functions of opacification, pigmentation, preventing blocking, reinforcement, etc. Fillers 26 having an average particle size of about 0.5 to 8 microns are typically suitable.

The thickness of the second layer 24 also constrains the weight percentage of fillers which may be added to the second layer 24. While filler concentrations exceeding 60 weight percent are possible with the multilayer film 20 of the present invention, the filler concentrations must be low enough to allow the particles 26 to be fully dispersed throughout the polymeric matrix of the second layer 24, and not stacked in a solid, relatively continuous fashion from the interface with first layer 22 to the outer surface of second layer 24. Filler concentrations of less than 15 weight percent are also feasible, but generally do not require the multilayer film 20 of this invention. Films having filler concentrations of less than 15 weight percent typically can be achieved by methods known in the prior art. However, disadvantages of filler concentrations of less than 15 percent, such as a harsh tactile sensation, can be overcome by providing the film of the present invention having a base layer 20 of very low filler concentration which is placed against the skin and a filler containing layer 24 which is shielded from the skin by the base layer 20.

The layers described above, must be joined, preferentially continuously, to yield a unitary multilayer film 20. Continuous joining of the layers ensures the material properties will be controlled by the first, or base layer 20. Because the filler containing polymeric opacifying layer 24 is brittle, due to the high concentration of fillers 26 present, the second layer 24 is difficult to independently manufacture and handle without tearing or shredding. Therefore, a preferred method to produce the multilayer film 20 is coextrusion.

It is important that the polymers selected for the first and second layers be compatible and self adhering to the other layer, to prevent problems in joining the two layers into a substantially continuous unitary multilayer film 20. If the layers are joined by coextrusion, it is furthermore important that the polymers of the two layers have somewhat closely matched melt indicies and melting points.

If the layers are not compatible and self adhering, a tie layer or compatiblizing layer (not shown) can be interposed between the base layer 22 and second layer 24. The compatiblizing or tie layer typically is a copolymer of the layers between which such layer is interposed and has properties intermediate those of the outer layers.

To coextrude the multilayer film 20 of the invention, having two layers, polymer resin containing pellets of the first layer 22 and 0 to 15 weight percent pigment, or other filler, containing pellets are provided and mixed in a hopper until a substantially homogeneous first mixture is obtained. To form the composition of second layer 24, polymer resin containing pellets of the second layer 24 and approximately 15 to approximately 60 weight percent filler 26 containing pellets 24 are provided. The filler 26 containing pellets may comprise one or more types of fillers 26, including pigments, when mixed with the polymer resin pellets of the second layer 24. The filler 26 containing pellets and second layer 24 polymer resin pellets are then mixed in a hopper until the filler and polymer resin pellets are substantially evenly dispersed in a substantially homogeneous second mixture.

The two homogeneous mixtures are fed into separate plasticating extruders coupled to a coextrusion feed block adapted to yield the desired proportion, typically approximately 9:1 of the first, or base, layer 22 to the second, or filler containing, layer 24. The mixtures are melted in the plasticating extruders and then simultaneously extruded through the coextrusion feed block under the conditions of pressure and temperature which are proper for the selected pellets, yielding a substantially continuous coextruded multilayer sheet having a cross section of the desired proportion of first layer 22 to second layer 24.

The substantially continuous multilayer sheet emerging from the coextrusion feed block is then fed into a coat hanger type film die, or other film die of rectangular cross section and adapted to maintain laminar flow, to yield a substantially continuous coextruded multilayer film having a thickness of less than or equal to about 0.5 mm (0.02 inches). The proportions of the layers are not changed as the multilayer film is extruded through the die and will remain in the selected proportion, say 9:1.

The substantially continuous multilayer film is then fed onto a rotating chill roll which causes freezing, or crystallization, of the multilayer film. The rotating chill roll should have a surface velocity equal to, or preferably greater, than that of the multilayer film as it emerges from the film die, so that no accumulation of the film occurs. This difference in relative surface velocities also results in additional thinning, or necking, of the sheet to a film of the desired finished thickness, typically less than about 0.25 mm (0.01 inches). The film, after leaving the chill roll, is then rolled or otherwise stored as convenient. Alternatively, the multilayer film can be fed directly into a secondary converting process.

An alternative to the coextrusion feed block and film die system, discussed above, is to utilize a coextrusion die in place of the coextrusion feed block and film die system. A coextrusion die receives the substantially homogeneous mixtures from the plasticating extruders, and coextrudes a multilayer film of the desired proportions, as described above, which is then fed onto the rotating chill roll.

A second process to produce the multilayer film of this invention is a coextruded blown film process. Two substantially homogenous mixtures are provided as described above and fed into plasticating extruders coupled to a coextrusion blown film die of circular cross section and having an annular orifice adapted to yield a proportion of first layer 22 to second layer 24 ranging of typically approximately 9:1. The two homogeneous mixtures are melted in the plasticating extruders and emerge from the lips of the die in a continuous vertical sheet, having the shape of a tapered hollow cylinder, which is drawn away from film die by pull rolls.

Gas or air is simultaneously fed through the film die, at a location internal the hollow cylinder, and into the continuous multilayer sheet, causing it to radially expand. As the continuous multilayer sheet rises it is cooled and frozen by heat transfer to the surrounding air. After solidifying, the multilayer sheet is collapsed and folded or rolled, then stored as desired.

The film according to either process above can be apertured by drawing such film against a forming screen by means of a vacuum and passing an air or water jet over the outwardly posited surface of the film. Such processes are described in U.S. Pat. No. 4,154,240 issued to Lucas et al., incorporated herein by reference. Alternatively, the film can be apertured prior to being fed onto the chill roll, as described in U.S. Pat. No. 4,552,709 issued to Koger, II et al., incorporated herein by reference.

While the foregoing examples of the coextrusion process are directed to a two layer multilayer film 20, it will be apparent to one skilled in the art that by adding a third homogeneous mixture, and adjusting the coextrusion feed block or film die of the plasticating extruder to produce a layered structure of the desired proportions, two types of three layer multilayer films are possible. A first type of a three layer multilayer film 120, illustrated in FIG. 2, has two outer base layers 122. Interposed between the outer base layers 122 is a central filler containing layer 124, having opposed first and second sides, each side substantially continuously joined to one side of one of the outer base layers 122. Similar to the foregoing two layer embodiment 20, central filler containing layer 124 is thin relative to the total thickness of multilayer film 120, comprising from about 5 to about 20 percent of the thickness of the multilayer film 120 and having about 15 to about 60 weight percent fillers 126 substantially uniformly dispersed therein.

Base layers 122 comprise in combination about 80 to about 95 percent of the film 120 thickness and may further comprise from about 1 to about 15 weight percent fillers (not shown) dispersed therein to increase the opacity, color or whiteness of the base layers 122. Base layers 122 may have the same or different compositions as required by the application. This three layer arrangement provides the advantage that either surface of multilayer film 120 can be made soft, compliant, and tactually pleasant to the skin, through the selection of materials, such as alpha-olefin polymers, for base layers 122.

Figure 3:
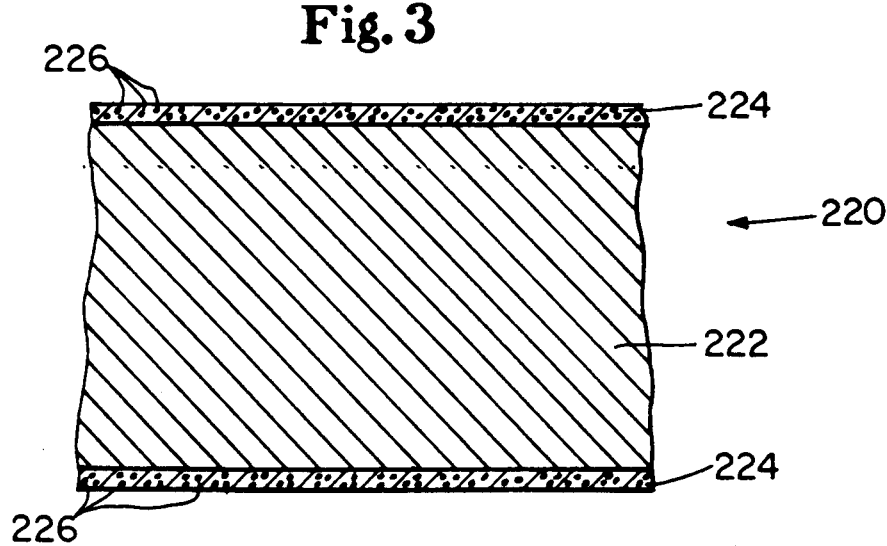
FIG. 3 is a cross sectional view of a third embodiment of the present invention having one central base layer between two outer filler containing layers.

A second type of three layer multilayer film 220, shown in FIG. 3, has two outer filler containing layers 224. Interposed between the filler containing layers 224 is a central base layer 222 having opposed first and second sides, each side substantially continuously joined to the outer layers 224. As described in the foregoing embodiments, the filler containing layers 224 have a combined thickness which is thin relative to the total multilayer film 220 thickness. The combined thickness of filler containing layers 224 is from about 5 to about 20 percent of the multilayer film 220 thickness. Each filler containing layer 224 has from about 15 to about 60 weight percent fillers 226 substantially uniformly dispersed therein. The outer layers 224 may have the same or different compositions, including the concentrations and types of fillers 226 or polymers, depending upon the application requirements.

Central base layer 222 comprises from about 80 to about 95 percent of the film 220 thickness. It is of course feasible to add about 1 to about 15 weight percent fillers to base layer 222 to increase its whiteness, or opacity, however, if central base layer 222 has filler containing layers 224 on either side with high opacifying pigment concentrations, base layer 222 will generally be hidden by the filler containing layers 224 and the benefits of any pigments added to base layer 222 will be less noticeable.

The multilayer film 220 of FIG. 3 has the advantage the both surfaces can be made to have a matte surface texture by selective incorporation of fillers, such as silica, into the outer filler containing layers 224 without the use of embossing rolls, as for example, when a blown film is produced. Alternatively, the two surfaces of multilayer film 220 can be made to differ in appearance, by incorporating different pigmentation into each of the outer layers 224.

Figure 2:
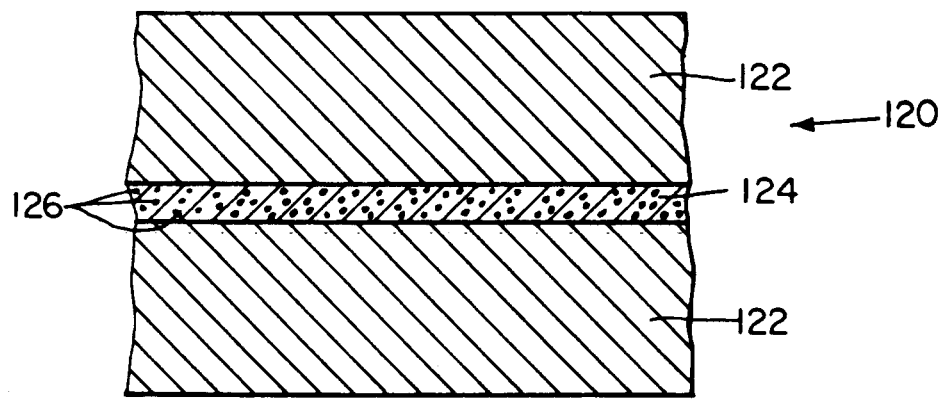
FIG. 2 is a cross sectional view of a second embodiment of the multilayer film of the present invention, having one central filler containing layer between two outer base layers.

It will be apparent that modified three layer structures having two juxtaposed base layers and a filler containing layer or two juxtaposed filler containing layers and a base layer may easily be constructed from the examples shown in FIGS. 2 and 3 respectively. Furthermore, four or more layer structures are possible and the two and three layer structures described above may be combined to give structures having multiple layers. However, the material properties, opacity, and processing of such multiple layer structures essentially conforms to that described above.

Exemplary, nonlimiting uses (not shown) for the multilayer films of this invention include diapers, adult incontinent products, catamenial pads and panty liners. A catamenial pad or panty liner can be made by providing 2 sheets of the multilayer film 20 of the invention, one apertured, using known techniques, to about 25 percent open area, and referred to as a topsheet, and one unapertured, referred to as a backsheet, each sheet having dimensions of about 20.3×7.6 cm (8 inches by 3 inches). The sheets can be made according to any of the material and filler combinations described above. One combination found to work well hiding stains and providing comfort to the wearer is an approximately 0.025 mm (0.001 inches) thick multilayer film 20 having a first layer 22 of low density polyethylene with approximately 4 weight percent titanium dioxide whitener dispersed therein, and a second layer 24 of ethylene vinyl acetate copolymer having about 25 weight percent silica and about 25 weight percent titanium dioxide dispersed therein. The base layer 22 comprises approximately nine-tenths of the total multilayer film 20 thickness and the filler containing opacifying layer 24 comprises about one-tenth of the total multilayer film 20 thickness. Also, an absorbent core, such as comminuted pulp or tissue wadding, having two opposed faces and dimensions of about 17.8×5.1×0.6 cm (7×2×0.25 inches) is used.

The topsheet and backsheet are placed in register on opposed faces of the absorbent core, then wrapped to enclose the core so that the topsheet and backsheet are affixed to or otherwise associated with opposed faces of the absorbant core. The seams, formed by the junctures of the topsheet and backsheet, are sealed using any known suitable means including adhesive bonding, ultrasonic welding or crimping, so long as the resultant seam is fluid tight. A panty liner is made in substantially the same manner, although the size of the absorbent core is reduced, as desired, to accommodate lesser amounts of vaginal discharge. The sizes of the topsheet and backsheet are reduced accordingly.

After the catamenial pad or panty liner is assembled, as described above, it is placed on the undergarment of the wearer with the apertured topsheet multilayer film 20 facing the skin and the unapertured backsheet multilayer film 20 oriented towards the undergarment. Vaginal discharge or menses will be deposited on the apertured topsheet, and drain to the absorbent core where such discharge or menses will be generally hidden by the opaque film of this invention. The discharge or menses will be retained in the core by the unapertured backsheet.

A diaper or adult incontinent product, having an absorbent core interposed between and affixed to, or otherwise associated with, an apertured topsheet, and an unapertured backsheet may be constructed and shaped to accommodate the waist and legs of the wearer, according to the teachings of U.S. Pat. No. 3,860,003 issued to Buell, which is incorporated herein by reference. Both the topsheet and backsheet of such a diaper or adult incontinent product may be advantageously constructed of the multilayer films of this invention.

It is recognized that various modifications to the invention can be made and various combinations of polymers and fillers, including those discussed above and others, can be utilized without departure from the spirit and scope of the invention.

What is claimed is:

1. A substantially void-free polymeric multilayer film which exhibits an opaque appearance without being stretched, said polymeric multilayer film comprising:
    (a) at least one relatively thick base layer comprised substantially of a polymer, said base layer having a thickness comprising at least about 80 percent of the total thickness of said multilayer film; and
    (b) at least one relatively thin filler containing polymeric layer substantially continuously joined to said base layer, said filler containing polymeric layer having about 15 to about 60 weight percent fillers substantially uniformly dispersed therein, said filler containing layer having a thickness not exceeding about 20 percent of the total thickness of said multilayer film, whereby said fillers in said relatively thin filler containing polymeric layer scatter the light rays incident upon said multilayer film to produce said opaque appearance in said multilayer polymeric film without significantly detracting from the material properties of said base layer.

2. A substantially void-free polymeric multilayer film which exhibits an opaque appearance without being stretched, said polymeric multilayer film comprising:
    (a) a first relatively thick outer base layer comprised substantially of a polymer;
    (b) a central relatively thin filler containing polymeric layer having a first side and a second side opposed thereto, said first side being substantially continuously joined to one side of said first outer base layer, said filler containing polymeric layer having about 15 to about 60 weight percent fillers substantially uniformly dispersed therein, and a thickness not exceeding about 20 percent of the total thickness of said multilayer film; and
    (c) a second relatively thick outer base layer comprised substantially of a polymer and having one side substantially continuously joined to said second side of said central filler containing layer, said first outer base layer and said second outer base layer together comprising at least about 80 percent of the total thickness of said multilayer film, whereby said fillers in said relatively thin filler containing polymeric layer scatter the light rays incident upon said multilayer film to produce said opaque appearance in said multilayer polymeric film without significantly detracting from the material properties of said base layers.

3. A substantially void-free polymeric multilayer film which exhibits an opaque appearance without being stretched, said polymeric multilayer film comprising:

(a) two relatively thin outer filler containing polymeric layers, each of said outer filler containing polymeric layers having about 15 to about 60 weight percent fillers substantially uniformly dispersed therein, said filler containing layers together having a combined thickness not exceeding about 20 percent of the total thickness of said multilayer film; and (b) a relatively thick central base layer having a first side and a second side opposed thereto and comprised substantially of a polymer, said base layer being interposed between said outer filler containing polymeric layers and having one of said outer filler containing polymeric layers substantially continuously joined to said first side of said base layer and the other of said outer filler containing layers substantially continuously joined to said second side of said base layer, said central base layer having a thickness comprising at least about 80 percent of the total thickness of said multilayer film, whereby said fillers in said relatively thin filler containing polymeric layers scatter the light rays incident upon said multilayer film to produce said opaque appearance in said multilayer polymeric film without significantly detracting from the material properties of said base layer.

4. A multilayer film according to claim 1, 2 or 3 wherein said filler containing layer comprises fillers selected from the group consisting of titanium dioxide, calcium carbonate, silica, colored pigments, filaments and combinations thereof.

5. A multilayer film according to claim 4 wherein said fillers impart opacity to said multilayer film.

6. A multilayer film according to claim 1, 2 or 3 wherein said filler containing layer comprises polymers selected from the group consisting of polyolefins, copolymers having at least one olefinic constituent, polyesters, nylons, copolymers of polyesters and nylons, and combinations thereof.

7. A multilayer film according to claim 6 wherein said filler containing layer comprises polymers selected from the group consisting of polyethylenes, polypropylenes, ethylene vinyl acetate copolymer and combinations thereof.

8. A multilayer film according to claim 1, 2 or 3 wherein said base layer comprises polymers selected from the group consisting of polyolefins, copolymers having at least one olefinic constituent, polyesters, nylons, copolymers of polyesters and nylons and combinations thereof.

9. A multilayer film according to claim 8 wherein said base layer comprises polymers selected from the group consisting of polyethylenes, polypropylenes and combinations thereof.

10. A multilayer film according to claim 8 further comprising from about 1 to about 15 weight percent fillers dispersed in said base layer.

11. A multilayer film according to claim 1 or 2 wherein said filler containing layer comprises from about 5 to about 20 percent of the thickness of the multilayer film.

12. A multilayer film according to claim 3 wherein said filler containing layers comprise from about 5 to about 20 percent of the thickness of the multilayer film.

13. A multilayer film according to claim 1, 2 or 3 further comprising apertures.

14. A multilayer film according to claims 11 or 12 wherein at least one of the sides of said multilayer film is white.

15. A multilayer film according to claim 11 or 12 wherein the opposite sides of said multilayer film are of different colors.

16. A multilayer film according to claim 11 or 12 wherein said outer layers comprise substantially different compositions.

17. A multilayer film according to claim 1, 2 or 3 wherein said multilayer film is placed in register with and associated with one face of an absorbant core having two opposed faces.

18. A multilayer film according to claim 17 further comprising apertures.

19. A multilayer film according to claim 17 further comprising a second multilayer film according to claim 17 placed in register with and associated with the opposed face of said absorbant core, one of said multilayer films associated with one face of said absorbant core further comprising apertures, whereby said multilayer films and said absorbant core are adapted for use as a panty liner, catamenial pad, diaper or adult incontinent product.

* * * * *

UNITED STATES PATENT AND TRADEMARK OFFICE
CERTIFICATE OF CORRECTION

PATENT NO. : 5,006,394
DATED : April 9, 1991
INVENTOR(S) : James C. Baird

It is certified that error appears in the above-identified patent and that said Letters Patent is hereby corrected as shown below:

Column 3, line 25, after "whitening" delete -- o -- .

Column 5, line 50, "homogenous" should read -- homogeneous -- .

Column 6, line 67, "the" should read -- that -- .

Column 7, line 49, "absorbant" should read -- absorbent -- .

Column 10, line 33, "absorbant" should read -- absorbent -- .

Column 10, line 40, "absorbant" should read -- absorbent -- .

Column 10, line 41, "absorbant" should read -- absorbent -- .

Column 10, line 43, "absorbant" should read -- absorbent -- .

Signed and Sealed this

Fifteenth Day of September, 1992

*Attest:*

DOUGLAS B. COMER

*Attesting Officer*     Acting Commissioner of Patents and Trademarks